United States Patent [19]
Richter et al.

[11] Patent Number: 5,922,005
[45] Date of Patent: Jul. 13, 1999

[54] STENT FABRICATION METHOD

[75] Inventors: Jacob Richter, Tel Aviv; Ira Yaron, Jerusalem, both of Israel

[73] Assignee: Medinol Ltd., Tel Aviv, Israel

[21] Appl. No.: 09/138,140

[22] Filed: Aug. 21, 1998

Related U.S. Application Data

[62] Division of application No. 08/742,422, Oct. 30, 1996, Pat. No. 5,836,964, which is a continuation of application No. 08/330,625, Oct. 27, 1994, abandoned.

[51] Int. Cl.$^6$ .................................................. A61M 29/00
[52] U.S. Cl. .......................................... 606/192; 128/898
[58] Field of Search .................................... 606/194, 198, 606/192, 191, 195; 623/1, 12; 128/989

[56] References Cited

U.S. PATENT DOCUMENTS

| | | |
|---|---|---|
| 5,443,500 | 8/1995 | Sigwart . |
| 5,449,373 | 9/1995 | Pinchasik et al. . |
| 5,449,382 | 9/1995 | Dayton . |
| 5,643,314 | 7/1997 | Carpenter et al. ...................... 128/898 |
| 5,755,734 | 5/1998 | Richter et al. ........................... 128/898 |
| 5,776,183 | 7/1998 | Kanesake et al. ....................... 606/198 |
| 5,810,872 | 9/1998 | Kanesake et al. ....................... 606/198 |

*Primary Examiner*—Michael Buiz
*Assistant Examiner*—Kevin Truong
*Attorney, Agent, or Firm*—Kenyon & Kenyon

[57] ABSTRACT

A stent and a method for fabricating the stent are disclosed. The stent has an originally flat pattern and connection points where the sides of the flat pattern are joined. The method includes the steps of a) cutting a stent pattern into a flat piece of metal thereby to produce a metal pattern, b) deforming the metal pattern so as to cause two opposing sides to meet, and c) joining the two opposing sides at least at one point. Substantially no portion of the stent projects into the lumen of the stent when the stent is expanded against the internal wall of a blood vessel.

26 Claims, 10 Drawing Sheets

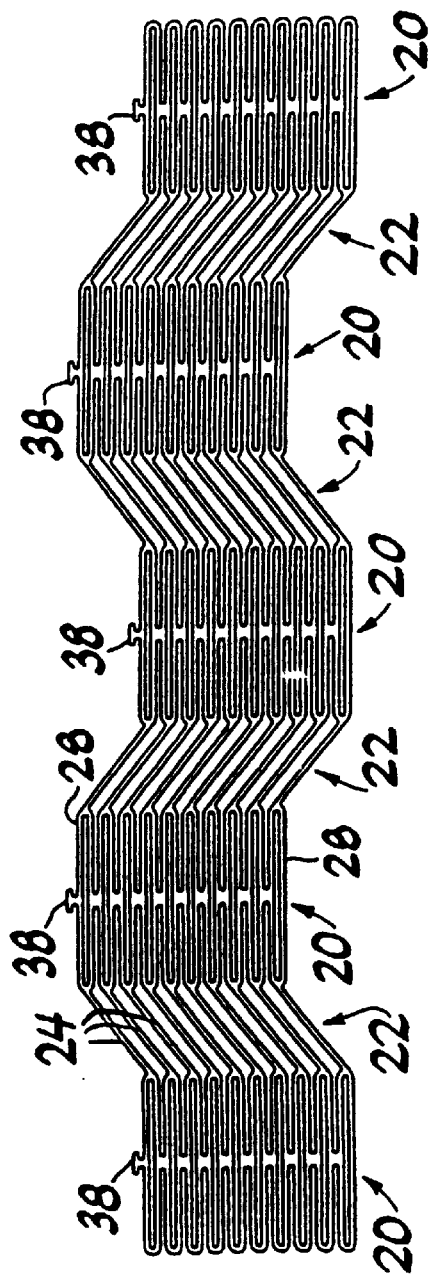
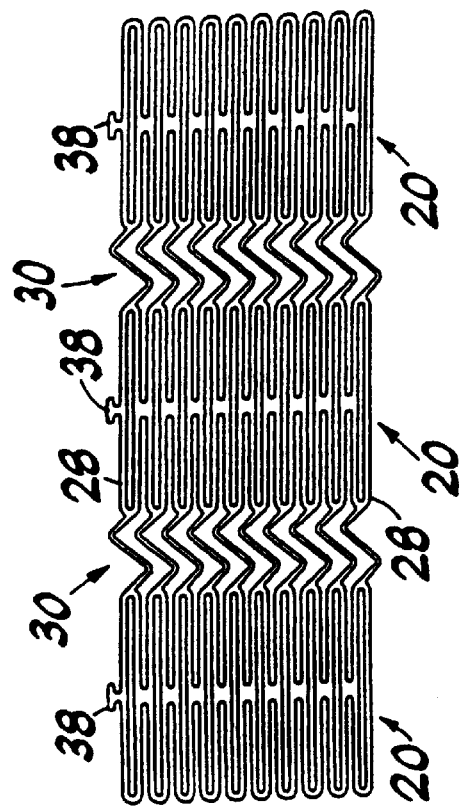
FIG. 2A
FIG. 2B

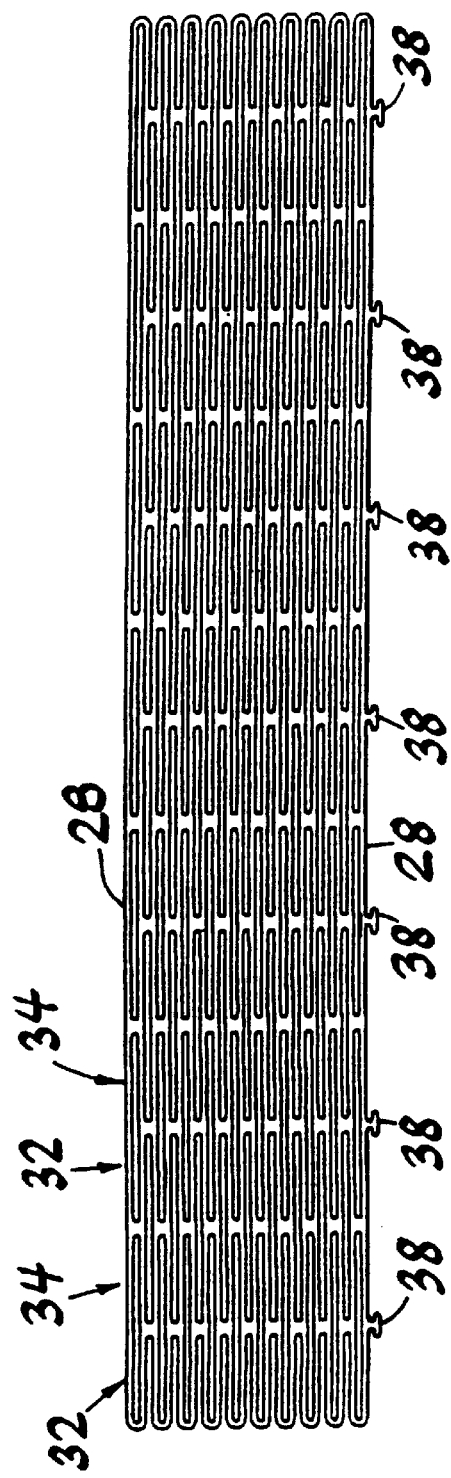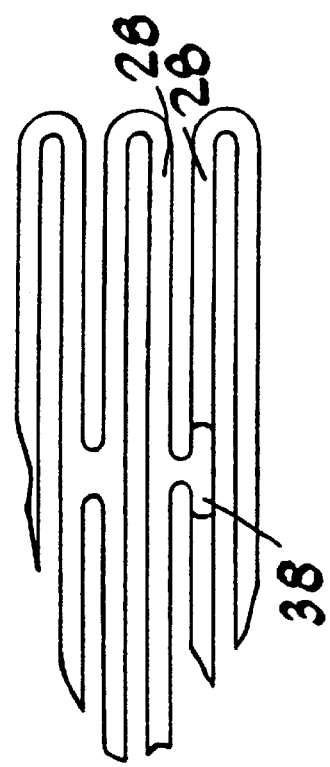

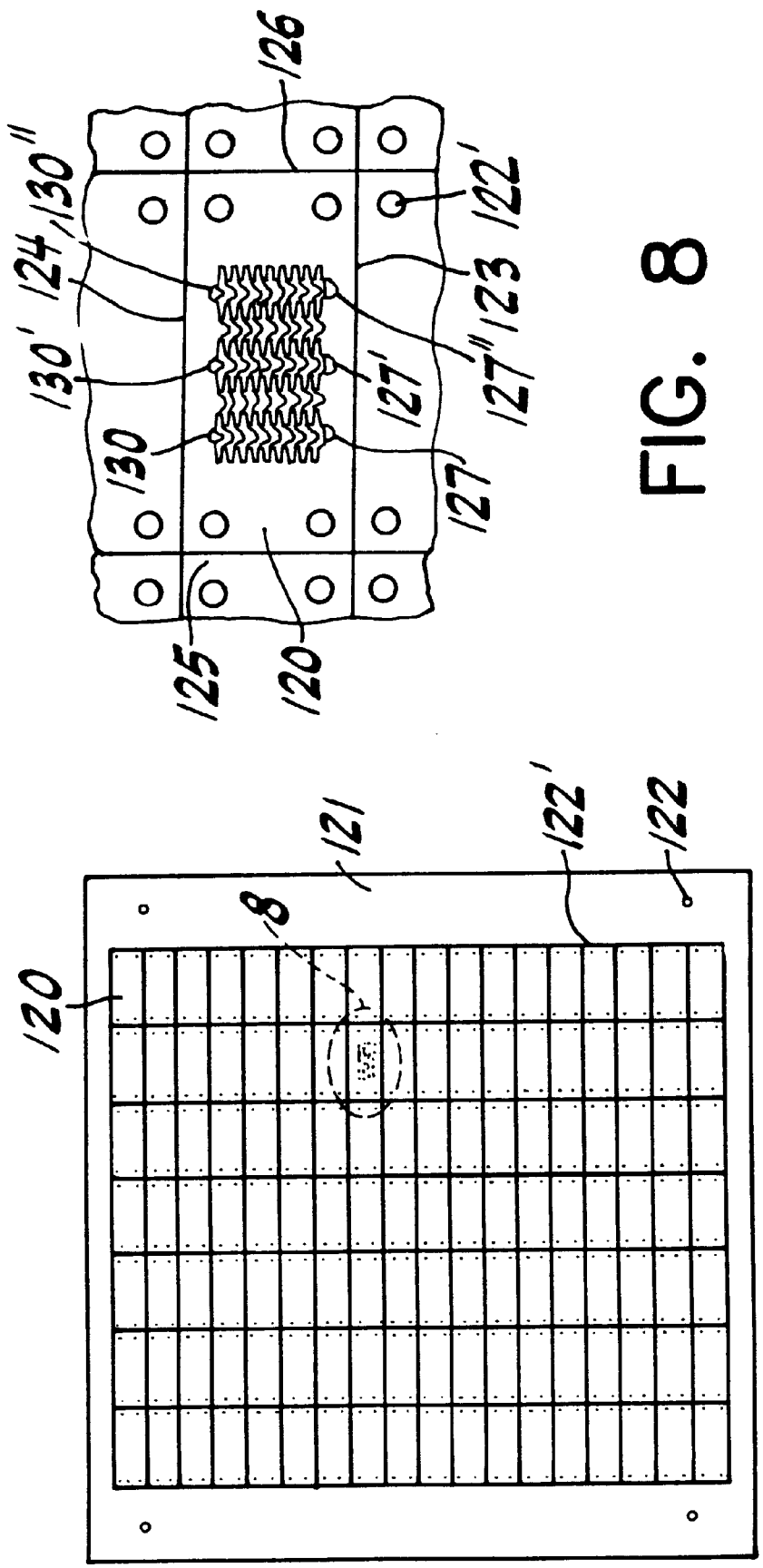

STENT FABRICATION METHOD

This application is a division of prior application Ser. No. 08/742,422 filed Oct. 30, 1996, now U.S. Pat. No. 5,836,964 which is a continuation of prior application No. 08/330,625 filed Oct. 27, 1994, now abandoned.

FIELD OF THE INVENTION

The present invention relates generally to methods of fabricating stents.

BACKGROUND OF THE INVENTION

Stents are known in the art. They are typically formed of a cylindrical metal mesh which can expand when pressure is internally applied. Alternatively, they can be formed of wire wrapped into a cylindrical shape.

As described in U.S. Pat. No. 4,776,337 to Palmaz, the cylindrical metal mesh shape is produced by laser cutting a thin walled metal tube. The laser cuts away all but the lines and curves of the mesh.

The method of U.S. Pat. No. '337 is applicable for relatively large mesh shapes and for meshes whose lines are relatively wide. However, for more delicate and/or intricate shapes, the spot size of the laser is too large.

SUMMARY OF THE PRESENT INVENTION

It is, therefore, an object of the present invention to provide a stent fabrication method which can produce stents with relatively intricate and/or delicate designs.

The method involves first creating a flat version of the desired stent pattern from a piece of thin sheet metal. The flat pattern can be produced through any suitable technique, such as etching the design into the sheet metal, or by cutting with a very fine laser, should one become commercially available or by any other technique.

Once the sheet metal has been cut, it is deformed so as to cause its edges to meet. To create a cylindrical stent from a flat, roughly rectangular metal pattern, the flat metal is rolled until the edges meet. The locations where edges meet are joined together, such as by spot welding. Afterwards, the stent is polished, either mechanically or electrochemically.

BRIEF DESCRIPTION OF THE DRAWINGS

The present invention will be understood and appreciated more fully from the following detailed description taken in conjunction with the drawings in which:

FIGS. 2A, 2B and 2C are illustrations of three alternative stent patterns to be etched, in accordance with the method of FIG. 1, into a flat sheet of metal;

FIGS. 5A and 5B are side and top view illustrations, respectively, of one connection location of the stent of FIG. 4;

FIG. 7 shows a piece of sheet metal with a plurality of patterns made in accordance with the invention;

FIG. 8 shows a detailed view of one of the patterns shown in FIG. 7;

DETAILED DESCRIPTION OF A PREFERRED EMBODIMENT

Figure 1:
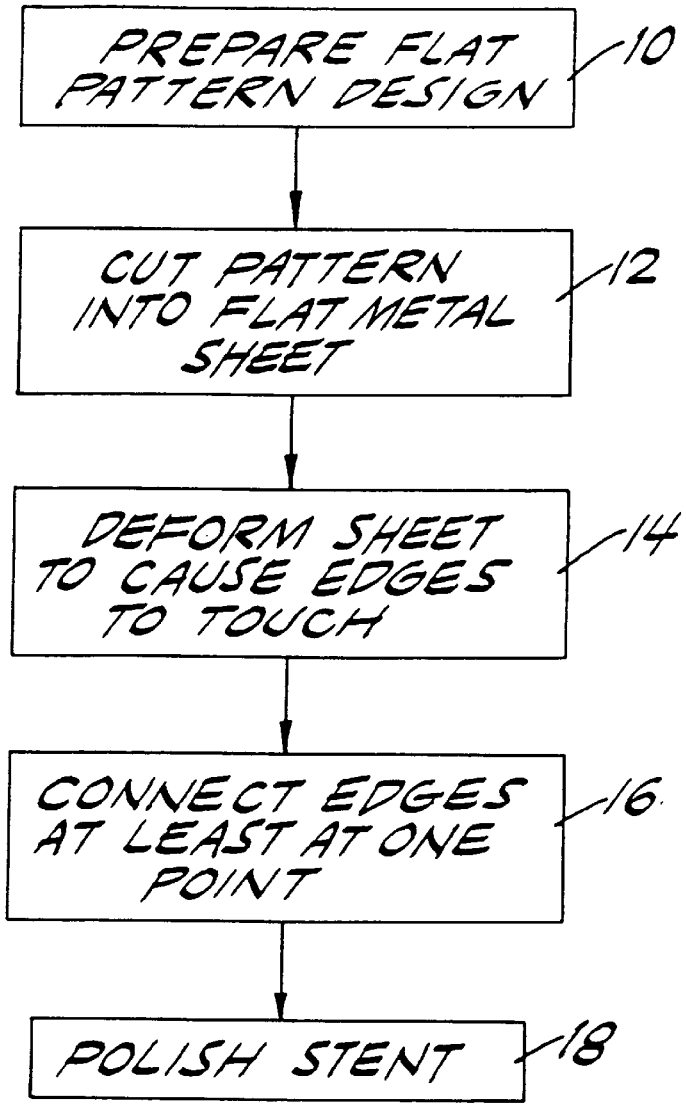
FIG. 1 is a flow chart illustration of the stent fabrication method of the present invention.

Reference is now made to FIG. 1, which illustrates the stent fabrication method of the present invention and to FIGS. 2A, 2B, 2C, 3 and 4 which are useful in understanding the method of FIG. 1.

In the stent fabrication method of the present invention, a stent designer first prepares a drawing of the desired stent pattern in a flat format (step 10).

FIGS. 2A, 2B and 2C illustrate three exemplary stent pattern designs. The pattern of FIG. 2A has two types of sections 20 and 22. Each section 20 has two opposing periodic patterns and each section 22 has a plurality of connecting lines 24. The pattern of FIG. 2A can be formed of any size; a preferable size is to have each section 20 be between 1 and 6 mm wide and each section 22 have connecting lines 24 of 1–6 mm long. At such sizes, the pattern of FIG. 2A cannot be cut using a laser cutting system.

The pattern of FIG. 2B is similar to that of FIG. 2A in that it also has sections 20 of opposing periodic patterns. The pattern of FIG. 2B also has connecting sections, labeled 30, which have a Z shape.

The pattern of FIG. 2C has no connecting sections. Instead, it has a series of alternating patterns, labeled 32 and 34.

The patterns of FIGS. 2A, 2B and 2C optionally also have a plurality of small protrusions 38 which are useful in forming the stent, as described hereinbelow.

Returning to FIG. 1, in step 12, the stent pattern is cut into a flat piece of metal ("sheet metal"). The metal can be any type of biocompatible material, such as stainless steel, or a material which is plated with a biocompatible material. The cutting operation can be implemented in any of a number of ways, such as by etching, or by cutting with a fine cutting tool, or by cutting with a very fine laser, should one become commercially available.

If step 12 is implemented with etching, then, the process is designed to cut through the sheet metal. This process is known; however, for the purposes of completeness, it will be briefly described hereinbelow.

The drawing of the pattern is reduced and printed onto a transparent film. Since it is desired to cut completely through the metal, the drawing is printed onto two films which are joined together in a few places along their edges. The sheet metal is covered, on both sides, with a layer of photoresist and placed between the two transparent, printed films. The structure is illuminated on both sides which causes the portions of the photoresist which receive the light (which are all the empty spaces in the pattern, such as spaces 26 of FIG. 2A) to change properties.

The sheet metal is placed into acid which eats away those portions of the photoresist which changes properties. The sheet metal is then placed into an etching solution which etches away all material on which there is no photoresist-removing solution which removes the photoresist, leaving the metal having the desired stent pattern.

Figure 3:
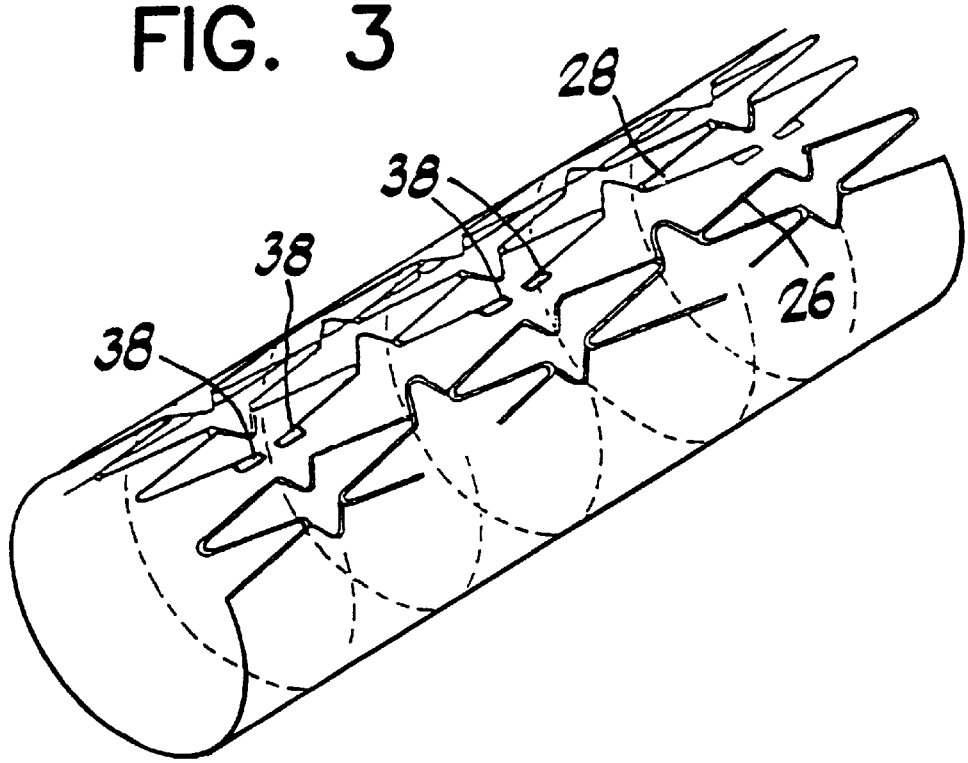
FIG. 3 is an isometric illustration of a stent being deformed, useful in understanding the method of FIG. 1.

In step 14, the metal pattern is deformed so as to cause its long sides (labeled 28 in FIGS. 2A, 2B and 2C) to meet each other. FIG. 3 illustrates the deformation process. For cylindrical stents, the deformation process is a rolling process, as shown.

Figure 5A:
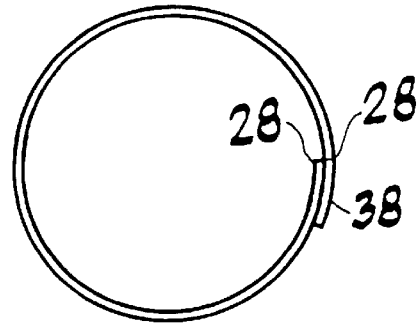

If the protrusions 38 have been produced, after deformation of the metal pattern, the protrusions 38 protrude over the edge 28 to which they are not attached. This is illustrated in FIG. 5A.

Figure 6:
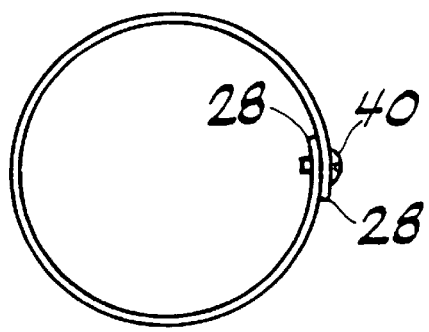
FIG. 6 is a side view illustration of one connection location of the stent of FIG. 4 which is connected in a nail-like manner.

In step 16, the edges 28 are joined together by any suitable process, such as spot welding. If the protrusions 38 were made, the protrusions 38 are joined to the opposite edge 28, either by welding, adhesive or, as illustrated in FIG. 6, with a nail-like element 40. FIG. 5B illustrates the connection of the protrusion to the opposite edge 28. Since protrusion 38 is typically designed to extend the width of one loop 39, the pattern in approximately preserved. This is seen in FIG. 5B.

Alternatively, the edges 28 can be brought together and joined in the appropriate places.

Figure 4:
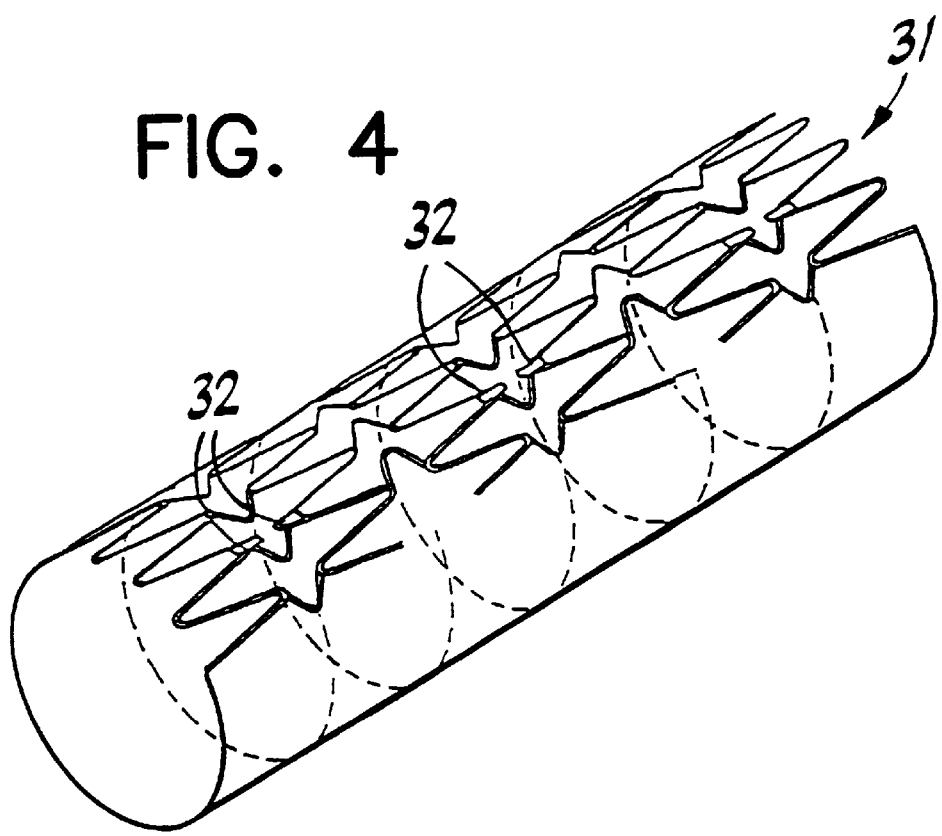
FIG. 4 is an isometric illustration of a stent formed from the method of FIG. 1.

FIG. 4 illustrates a stent 31 formed by the process of steps 10–16 for the pattern of FIG. 2A. It is noted that such a stent has connection points 32 formed by the joining of the points 30.

Finally, the stent 31 is polished to remove any excess material not properly removed by the cutting process (step 12). The polishing can be performed mechanically, by rubbing a polishing stick having diamond dust on its outside inside the stent 31. Alternatively, an electropolishing unit can be utilized.

FIG. 7 shows an alternative embodiment of the invention in which a plurality of patterns 120 are etched and cut into the sheet metal 121 as previously discussed. FIG. 8 is an enlarged view of one of the plurality of patterns 120 shown in FIG. 7.

Figure 10:
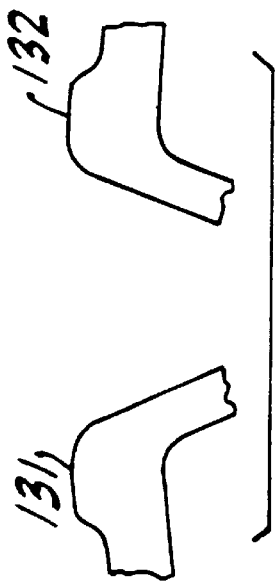
FIG. 10 shows a detailed view of a pair of engaging protrusions shown in FIG. 8.
Figure 9:
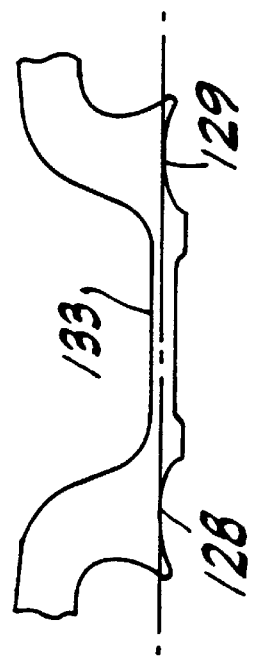
FIG. 9 shows a detailed view of a pair of engagement troughs shown in FIG. 8.

FIG. 9 is an enlarged view of one pair 127 of the plurality of engagement troughs 128 and 129 shown in FIG. 8. FIG. 10 is an enlarged view of one pair 130 of the plurality of engagement protrusions 131 and 132 shown in FIG. 8. The sheet metal 121 and each of the patterns 120 is provided with a plurality of alignment apertures 122 and 122' adapted to receive sprockets (not shown) for precisely moving and maintaining the precise alignment of the sheet metal 121 and the patterns 120 during the various stages of manufacturing. Each pattern 120 has a first long side 123 and a second long side 124, a first short side 125, and a second short side 126. The first long side 123 is provided with a plurality of pairs 127, 127' and 127" of engagement troughs 128 and 129 (shown in greater detail in FIG. 9). Each pair 127, 127' and 127" of engagement troughs has a first engagement trough 128 and a second engagement trough 129. The second long side 124 is provided with a plurality of pairs 130, 130' and 130" of engagement protrusions (shown in greater detail in FIG. 10). Each pair 130, 130' and 130" of engagement protrusions is provided with a first engagement protrusion 131 and a second engagement protrusion 132. The pairs of engagement protrusions 130, 130' and 130" are disposed substantially opposite the pairs of engagement troughs 127, 127' and 127".

Figure 19:
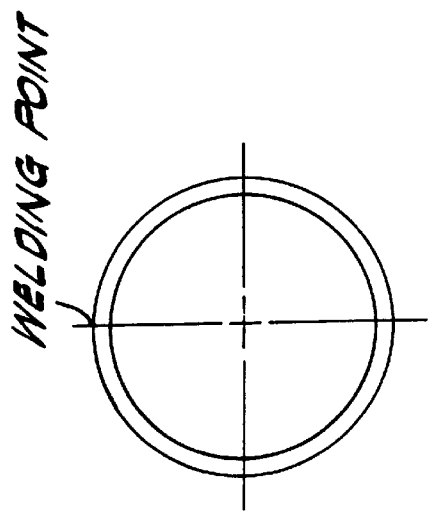
FIG. 19 is a cross-sectional view of a stent constructed in accordance with this invention.
Figure 20:
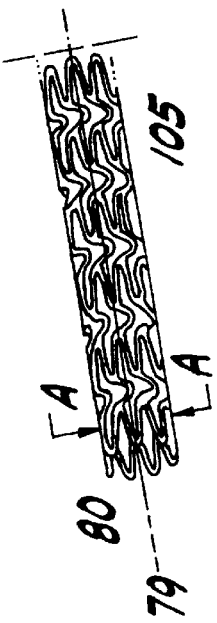
FIG. 20 is a perspective view of a stent constructed in accordance with this invention.
Figure 16:
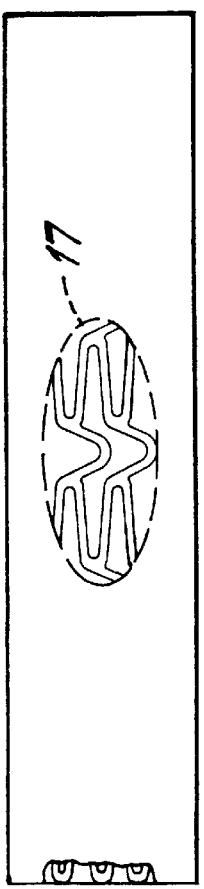
FIG. 16 shows a cell of a stent made in accordance with this invention.
Figure 18:
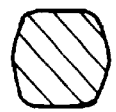
FIG. 18 is a cross-sectional view of a longitudinal member of a stent constructed in accordance with this invention.
Figure 17:
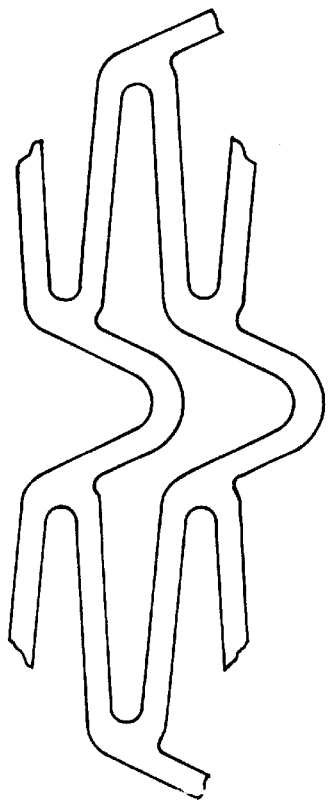
FIG. 17 is an enlarged view of the cell shown in FIG. 16.

The engagement troughs 128 and 129 are disposed and adapted to receive and engage the engagement protrusions 131 and 132 so that the alignment of the stent is maintained when the pattern 120 is deformed and the flat sheet metal is rolled so that the first long side 123 and the second long side 124 meet each other to form a tube as shown in FIGS. 19 and 20.

A bridge 133 of material is disposed between each pair 127, 127' and 127" of engagement troughs 128 and 129. This bridge 133 imparts additional stability and facilitates alignment during manufacturing and imparts additional strength to the welds of the finished stent as discussed below.

Figure 12:
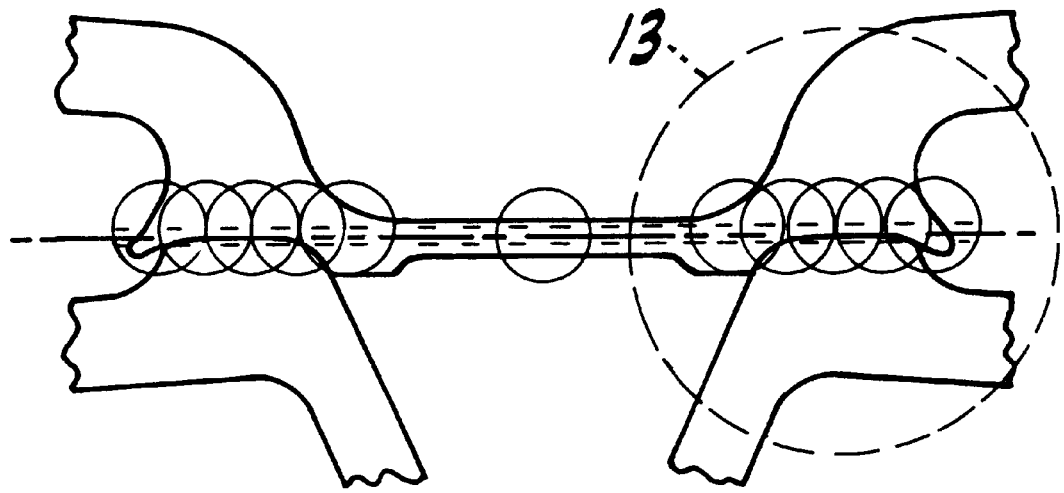
FIG. 12 shows a welding run practiced in accordance with the invention.
Figure 13:
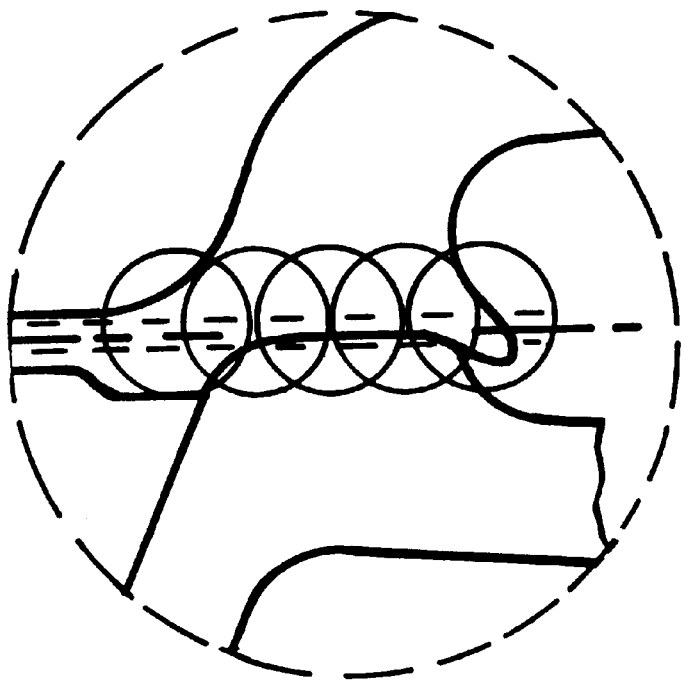
FIG. 13 is a detailed view of the welding run shown in FIG. 12.

After the sheet has been rolled into a tubular stent and the engagement troughs 128 and 129 have received the engagement protrusions 131 and 132, means (not shown) are utilized to maintain the alignment and the bridge 133 is cut to leave two substantially equal parts. The bridge 133 may be cut in a variety of ways well known to those skilled in the art, however, in a preferred embodiment, a laser is utilized. Engagement trough 128 is welded to engagement protrusion 131 and engagement trough 129 is welded to engagement protrusion 132 as shown in FIGS. 12 and 13. This may be accomplished in a variety of ways well known to those skilled in the art, however, in a preferred embodiment a plurality of spot welds are utilized. In an especially preferred embodiment, about five spot welds are used in each weld run as shown in FIGS. 12 and 13. The heat produced by the welding melts the cut bridge 133 material and the material is drawn towards the engagement trough 128 or 129 to which the material is attached and is drawn into the welded area between the engagement trough and the engagement protrusion where the additional bridge material becomes part of and imparts additional strength to the weld. The stent may then be finished as previously discussed.

FIG. 13 is an enlarged view of the welded area shown in FIG. 12. In a preferred embodiment, the weld run is offset from the point where the engagement trough and the engagement protrusion contact each other. In an especially preferred embodiment, the weld run is offset about 0.01 mm.

Figure 14:
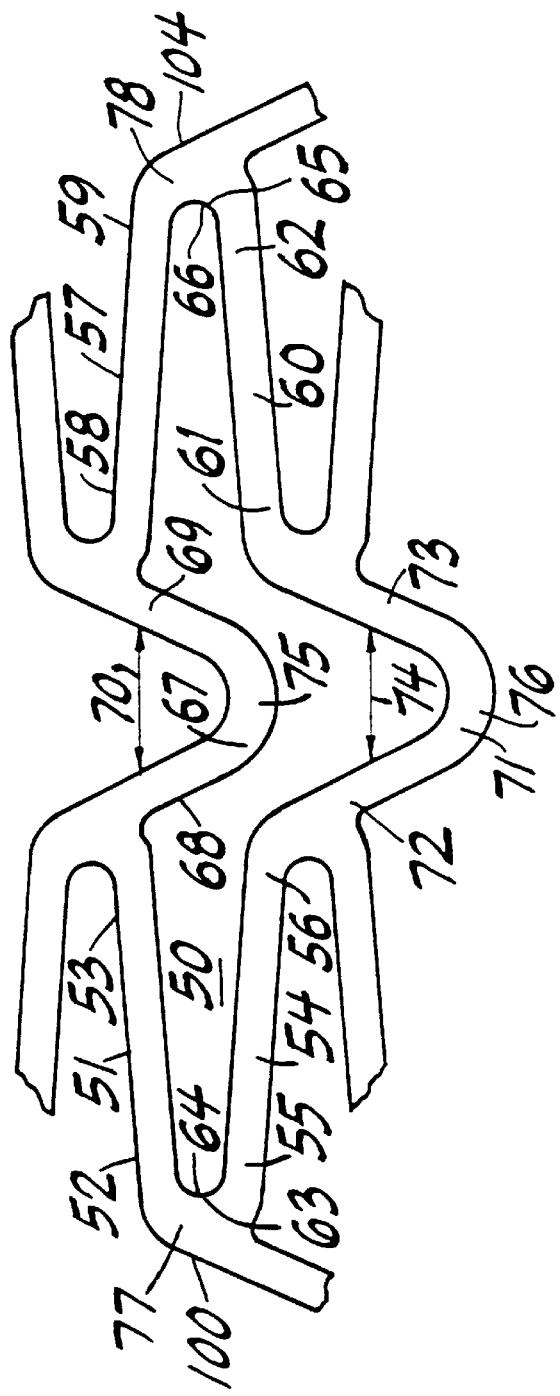
FIG. 14 is a detailed view of a cell of a stent made in accordance with this invention.

FIG. 14 is a detailed view of the pattern shown in FIG. 8. As shown in FIGS. 14 and 20, Applicants' invention can also be described as an expandable stent defining a longitudinal aperture 80 having a longitudinal axis or extension 79 and a circumferential axis or extension 105, including a plurality of flexible connected cells 50 with each of the flexible cells 50 having a first longitudinal end 77 and a second longitudinal end 78. Each cell 50 also is provided with a first longitudinal apex 100 disposed at the first longitudinal end 77 and a second longitudinal apex 104 disposed at the second longitudinal end 78. Each cell 50 also includes a first member 51 having a longitudinal component having a first end 52 and a second end 53; a second member 54 having a longitudinal component having a first end 55 and a second end 56; a third member 57 having a longitudinal component having a first end 58 and a second end 59; and a fourth member 60 having a longitudinal component having a first end 61 and a second end 62. The stent also includes a first loop 63 defining a first angle 64 disposed between the first end 52 of the first member 51 and the first end 55 of the second member 54. A second loop 65 defining a second angle 66 is disposed between the second end 59 of the third member 57 and the second end 62 of the fourth member 60 and is disposed generally opposite to the first loop 63. A first flexible compensating member or flexible link 67 having a first end 68 and a second end 69 is disposed between the first member 51 and the third member 57 with the first end 68 of the first flexible compensating member or flexible link 67 communicating with the second end 53 of the first member 51 and the second end 69 of the first flexible compensating member or flexible link 67 communicating with the first end 58 of the third member 57. The first end 68 and the second end 69 are disposed a variable longitudinal distance 70 from each other. A second flexible compensating member 71 having a first end 72 and a second end 73 is disposed between the second member 54 and the fourth member 60. The first end 72 of the second flexible compensating member or flexible link 71 communicates with the second end 56 of the second member 54 and the second end 73 of the second flexible compensating member or flexible link 71 communicates with the first end 61 of the fourth member 60. The first end 72 and the second end 73 are disposed a variable longitudinal distance 74 from each other. In a preferred embodiment, the first and second flexible compensating member or flexible links 67 and 71 are arcuate. The first and second flexible compensating member or flexible links 67 and 71 are differentially extendable or compressible when the stent is bent in a curved direction away from the longitudinal axis 79 of the aperture 80. (Shown in FIG. 20.) The first member 51, second member 54, third member 57, and fourth member 60 and the first loop 63 and the second loop 65 and the first flexible compensating member or flexible link 67 and the second flexible compensating member or flexible link 71 are disposed so that as the stent is expanded the distance between the first flexible compensating member or flexible link 67 and the second flexible compensating member or flexible link 71 increases and the longitudinal component of the first member 51, second member 54, third member 57 and fourth member 60 decreases while the first loop 63 and the second loop 65 remain generally opposite to one another, the ends 68 and 69 of the first flexible compensating member or flexible link 67 and the ends 72 and 73 of the second flexible compensating member or flexible link 71 open so as to increase the variable longitudinal distance 70 between the first end 68 and the second end 69 of the first flexible compensating member or flexible link 67 and so as to increase the variable longitudinal distance 74 between the first end 72 and the second end 73 of the second flexible compensating member or flexible link 71. This compensates for the decreasing of the longitudinal component of the first member 51, second member 54, third member 57, and fourth member 60 and substantially lessens the foreshortening of the stent upon its expansion. Upon expansion, the first flexible compensating member 67 and the second flexible compensating member 71 impart support to the lumen being treated.

Figure 15:
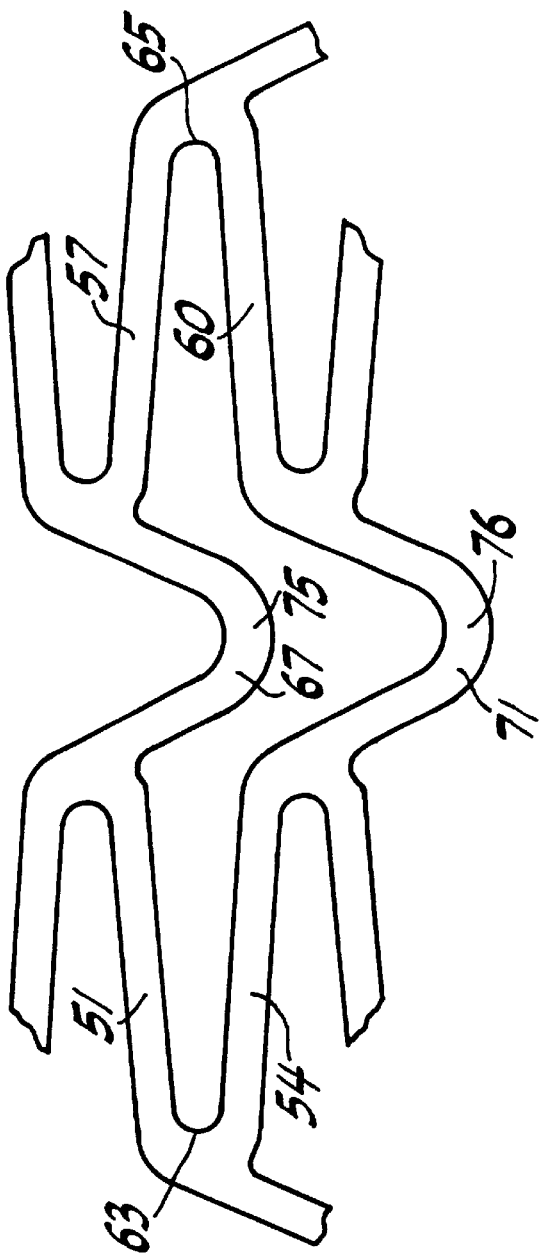
FIG. 15 is a detailed view of a cell made in accordance with this invention.
Figure 11:
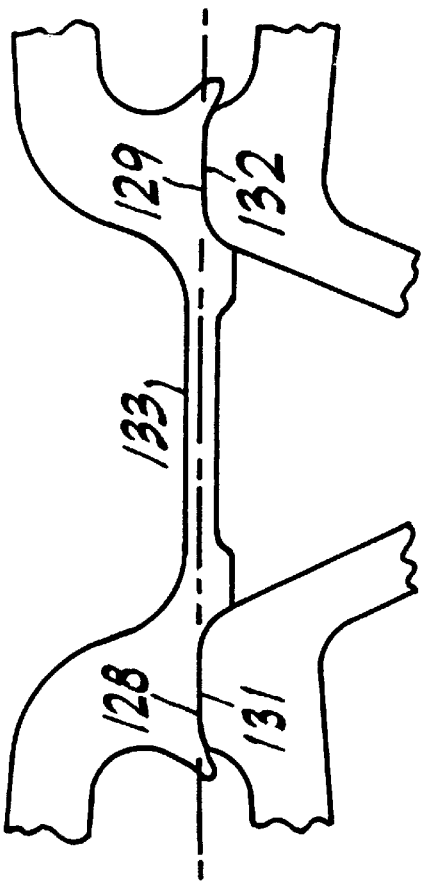
FIG. 11 shows the engagement troughs and engagement protrusions of FIGS. 9 and 10 in the engaged position.

FIG. 15 shows the dimensions of an especially preferred embodiment of this invention. The deflection points, i.e., the first and second loops 63 and 65 and the first and second compensating members 67 and 71, are made wider than the first, second, third, and fourth members 51, 54, 57 and 60 so that the force of the deflection is distributed over a wider area upon the expansion of the stent. The deflection points can be made wider than the first, second, third and fourth members in differing amounts so that the deflection will occur in the narrower areas first due to the decreased resistance. In a preferred embodiment, the first and second compensating members are wider than the first, second, third and fourth members and the first and second loops are wider than the first and second compensating members. One of the advantages of sizing the first and second loops so that they are wider than the first and second compensating members is that the stent will substantially compensate for foreshortening as the stent is expanded. In the embodiment shown in FIG. 15, the first, second, third and fourth members 51, 54, 57 and 60 have a width of about 0.1 mm. The first and second loops 63 and 65 have a width of about 0.14 mm. The first and second compensating members 67 and 71 are provided with a thickened portion 75 and 76 having a width of about 0.12 mm. Thus, in this especially preferred embodiment, the first and second loops have a width that is about 40% greater and the first and second compensating members have a width that is about 20% greater than the width of the first, second, third and fourth members.

FIGS. 16 through 20 show details of a stent constructed in accordance with this invention.

Yet another advantage of Applicant's invention is shown in FIGS. 21 to 24. For the sake of clarity, the dimensions and the degree of displacement of the components of the stents shown in FIGS. 21 to 24 has been intentionally exaggerated.

Figure 22:
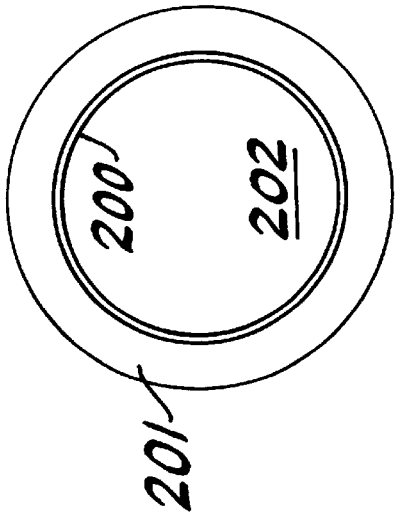
FIG. 22 is a cross-sectional front view of the stent shown in FIG. 21 after it has been expanded.
Figure 21:
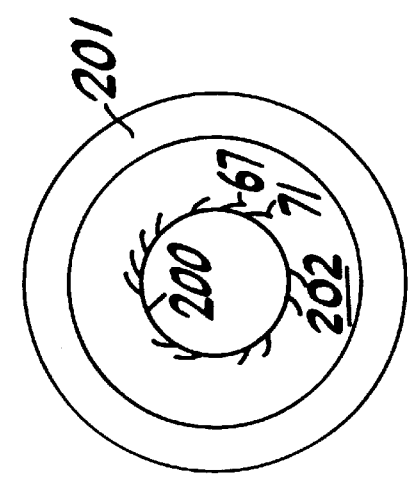
FIG. 21 is a cross-sectional front view of an unexpanded stent made in accordance with the invention.

FIG. 21 is a cross-sectional front view taken along line A—A of the unexpanded stent made in accordance with applicants invention shown in FIG. 20. The unexpanded stent 200 of FIG. 21 is shown disposed in the lumen 202 of a blood vessel 201 prior to expansion. As previously discussed, this stent is made by first cutting the stent pattern into a flat piece of sheet metal and then rolling the sheet metal into a tube to form the tubular stent. As shown in FIG. 21 after rolling, the first and second flexible compensating members 67 and 71 of the unexpanded stent tend to "flare out" in a direction away from the longitudinal axis or lumen of the stent. Thus, the flexible compensating members 67 and 71 define outer diameters which are larger than the outer diameters defined by the remaining portions of the stent. FIG. 22 shows the stent of FIG. 21 after it has been expanded in the lumen and against the internal wall of the blood vessel. As shown in FIG. 22, upon expansion of the unexpanded stent toward the wall of the blood vessels, the walls of the blood vessel imparts a mechanical force to the first and second flexible compensating members 67 and 71 and the compensating members move toward the longitudinal axis or lumen of the stent until they are substantially in registry with the remaining portion of the stent. Thus, the lumen of the expanded stent is substantially circular when viewed in cross section with substantially no portion of the expanded stent projecting into the lumen or towards the longitudinal axis of the expanded stent.

Figure 23:
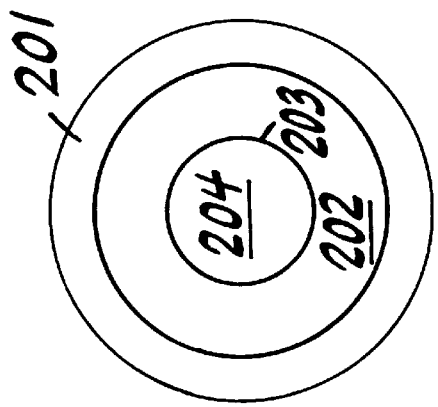
FIG. 23 is a cross-sectional front view of an unexpanded stent made by cutting a pattern in a tube.

FIG. 23 is similar to FIG. 21 except that the pattern has been cut into a tubular member using conventional methods of making stents. As shown in FIG. 23, the flexible compensating members do not flare out away from the longitudinal axis of the unexpanded stent 203. Upon the expansion of the stent shown in FIG. 23 toward the walls of the blood vessel 201, the flexible compensating members 67' and 71' tend to "flare in" and project into the lumen 204 of the expanded stent 203.

Figure 24:
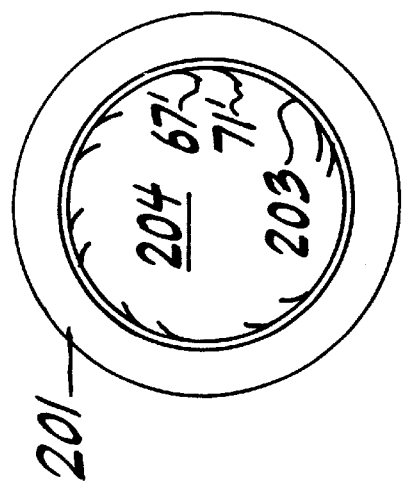
FIG. 24 is a cross-sectional front view of the stent shown in FIG. 23 after expansion.

FIG. 24 shows the stent 203 of FIG. 23 after it has been expanded in a lumen 204 of a blood vessel 201. The flexible compensating members 67' and 71' are not in registry with the remaining portions of the stent and define a diameter smaller than the diameter of remaining portions of the stent. These projections into the lumen of the stent create turbulence in a fluid flowing through the longitudinal axis of the expanded stent and could result in clot formation.

It will be appreciated by persons skilled in the art that the present invention is not limited to what has been particularly shown and described hereinabove. Rather the scope of the present invention is defined only by the claims which follow.

We claim:

1. A method of fabricating a stent comprising the steps of:
   a) cutting a plurality of stent patterns into a flat piece of metal sheet, each of said patterns having a first long side and a second long side, said first long side provided with a plurality of pairs of engagement troughs, said second long side provided with a plurality of pairs of engagement protrusions, said plurality of pairs of engagement troughs and said plurality of pairs of engagement protrusions disposed substantially opposite each other, each of said plurality of pairs of said engagement troughs comprising a first engagement trough and a second engagement trough, said first and second engagement troughs sized and disposed to receive and engage said engagement protrusions when said pattern are deformed and rolled into a tubular shape, each pair of said engagement troughs provided with a bridge disposed between said first engagement trough and said second engagement trough;
   b) providing said flat metal sheet with a plurality of alignment apertures;
   c) deforming said patterns into a tubular shape so that said pairs of engagement troughs engage said pairs of engagement protrusions;
   d) cutting said bridge; and
   e) attaching each of said engagement troughs to each of said engagement protrusions with which it is engaged, to form said stent.

2. The method of claim 1, wherein step d) is carried out using a laser.

3. The method of claim 1, wherein step e) is carried out utilizing a weld.

4. The method of claim 3, wherein step e) is carried out using a welding run that is offset from the point where said engagement troughs and said engagement protrusions contact each other.

5. The method of claim 4, wherein said welding run is offset about 0.01 mm from the point where said engagement troughs and said engagement protrusions contact each other.

6. The method of claim 3, wherein said weld is a spot weld.

7. The method of claim 6, wherein a plurality of spot welds is utilized.

8. The method of claim 7, wherein 5 spot welds are utilized.

9. The method of claim 1, wherein step e) is carried out utilizing an adhesive.

10. The method of claim 1, wherein step e) is carried out utilizing a nail-like element.

11. The method of claim 1, said stent defining a longitudinal lumen wherein substantially no portion of said stent projects into said longitudinal lumen upon expansion of said stent against the internal wall of a vessel.

12. A method of fabricating a stent comprising the steps of:
   a) cutting a plurality of stent patterns into a flat piece of metal, each of said patterns comprising a plurality of flexible connected cells, each of said flexible cells comprising:
      a) a first member having a longitudinal component having a first end and a second end;
      b) a second member having a longitudinal component having a first end and a second end,
      c) a third member having a longitudinal component having a first end and a second end;
      d) a fourth member having a longitudinal component having a first end and a second end;
      e) a first loop defining a first angle disposed between said first end of said first member and said first end of said second member;
      f) a second loop defining a second angle disposed between said second end of said third member and said second end of said fourth member, and disposed generally opposite to said first loop;
      g) a first flexible compensating member or flexible link having a first end and a second end disposed between said first member and said third member, said first end of said first flexible compensating member or flexible link communicating with said second end of said first member and said second end of said first flexible compensating member or flexible link communicating with said first end of said third member, said first and said second ends of each of said first, second, third, and fourth members disposed a variable longitudinal distance from each other;
      h) a second flexible compensating member or flexible link having a first end and a second end disposed between said second member and said fourth member, said first end of said second flexible compensating member or flexible link communicating with said second end of said second member and said second end of said second flexible compensating member or flexible link communicating with said first end of said fourth member, said first and said second ends of each of said first, second, third, and fourth members disposed a variable longitudinal distance from each other, said first and said second flexible compensating member or flexible links differentially extendable or compressible when said stent is bent in a curved direction away from the longitudinal axis of said aperture; and
      i) said first, said second, said third, and said fourth members and said first and said second loops, and said first and said second flexible compensating member or flexible links disposed so that as said stent is expanded the distance between said first and said second flexible compensating member or flexible links increases and the longitudinal component of said first, second, third and fourth members decreases while said first and said second loops remain generally opposite to one another, the ends of said first and said second flexible compensating member or flexible links open so as to increase said variable longitudinal distance between said first and said second ends of said first flexible compensating member or flexible link and so as to increase said variable longitudinal distance between said first and said second ends of said second flexible compensating member or flexible link so as to compensate for the decreasing of the longitudinal component of said first, second, third, and fourth members and substantially lessen the foreshortening of said stent upon its expansion;

each of said plurality of stent patterns having a first long side and a second long side, said first long side provided with a plurality of pairs of engagement troughs, said second long side provided with a plurality of pairs of engagement protrusions, said plurality of pairs of engagement troughs and said plurality of pairs of engagement protrusions disposed substantially opposite each other, each of said plurality of pairs of said engagement troughs comprising a first engagement trough and a second engagement trough, said first and second engagement troughs sized and disposed to receive and engage said engagement protrusions when said pattern are deformed and rolled into a tubular shape, each pair of said engagement troughs provided with a bridge disposed between said first engagement trough and said second engagement trough;

b) deforming said patterns into a tubular shape so that said pairs of engagement troughs engage said pairs of engagement protrusions;

c) cutting said bridge; and d) attaching each of said engagement troughs to each of said engagement protrusions with which it is engaged, to form said stent.

13. The method of claim 12, further comprising the step of providing said flat metal sheet with a plurality of alignment apertures.

14. The method of claim 12, wherein said first loop, said second loop, said first compensating member, and said second compensating member are wider than said first, second, third and fourth members.

15. The method of claim 14, wherein said first and said second compensating members are wider than said first, second, third, and fourth members and said first and said second loops are wider than said first and said second compensating members.

16. The method of claim 15, wherein said first and said second loops have a width that is about 40% greater than the width of said first, second, third, and fourth members and said first and said second compensating members have a width that is about 20% greater than the width of said first, second, third, and fourth members.

17. The method of claim 12, wherein step c) is carried out using a laser.

18. The method of claim 12, wherein step d) is carried out utilizing a weld.

19. The method of claim 18, wherein step d) is carried out utilizing a welding run that is offset from the point where said engagement troughs and said engagement protrusions contact each other.

20. The method of claim 19, wherein said welding run is offset about 0.01 mm from the point where said engagement troughs and said engagement protrusions contact each other.

21. The method of claim 18, wherein said weld is a spot weld.

22. The method of claim 21, wherein a plurality of spot welds is utilized.

23. The method of claim 22, wherein 5 spot welds are utilized.

24. The method of claim 12, wherein step d) is carried out utilizing an adhesive.

25. The method of claim 12, wherein step d) is carried out utilizing a nail-like element.

26. The method of claim 12, said stent defining a longitudinal lumen wherein substantially no portion of said stent projects into said longitudinal lumen upon expansion of said stent against the internal wall of a vessel.

* * * * *